United States Patent
Drummy et al.

(10) Patent No.: US 9,933,375 B2
(45) Date of Patent: Apr. 3, 2018

(54) XRF/XRD SYSTEM WITH DYNAMIC MANAGEMENT OF MULTIPLE DATA PROCESSING UNITS

(71) Applicants: Michael Drummy, Reading, MA (US); C. Tricia Liu, Weston, MA (US)

(72) Inventors: Michael Drummy, Reading, MA (US); C. Tricia Liu, Weston, MA (US)

(73) Assignee: Olympus Scientific Solutions Americas, Inc., Waltham, MA (US)

( * ) Notice: Subject to any disclaimer, the term of this patent is extended or adjusted under 35 U.S.C. 154(b) by 191 days.

(21) Appl. No.: 14/865,827

(22) Filed: Sep. 25, 2015

(65) Prior Publication Data
US 2017/0089847 A1    Mar. 30, 2017

(51) Int. Cl.
G01N 23/22    (2018.01)
G01N 23/223    (2006.01)

(52) U.S. Cl.
CPC ........... *G01N 23/223* (2013.01); *G01N 23/22* (2013.01)

(58) Field of Classification Search
CPC ............................. G01N 23/22; G01N 23/223
USPC ........................................................ 378/44–50
See application file for complete search history.

(56) References Cited

U.S. PATENT DOCUMENTS

| | | | | |
|---|---|---|---|---|
| 5,299,138 A * | 3/1994 | Fiori | ................ | G01N 23/20091 250/390.07 |
| 6,563,902 B2 * | 5/2003 | Takahashi | ............ | G01N 23/223 378/115 |
| 7,430,273 B2 * | 9/2008 | Yellepeddi | ............. | G01N 21/67 378/44 |
| 7,587,025 B2 * | 9/2009 | Fukai | ................... | G01N 23/223 378/149 |
| 7,623,625 B2 * | 11/2009 | Boyden | ................ | G01N 23/201 378/86 |
| 7,623,627 B2 * | 11/2009 | Matoba | ................ | G01N 23/223 378/58 |
| 7,889,335 B2 * | 2/2011 | Durst | ........................ | G01J 3/02 356/326 |
| 7,916,834 B2 * | 3/2011 | Piorek | .................. | G01N 23/223 378/102 |
| 7,970,101 B2 * | 6/2011 | Sakai | ................... | G01N 23/223 378/44 |
| 8,000,439 B2 * | 8/2011 | Matoba | ................ | G01N 23/223 378/44 |
| 8,155,268 B2 * | 4/2012 | Pesce | .................... | G01N 23/223 378/45 |

(Continued)

OTHER PUBLICATIONS

Ron Jenkins, An Introduction to X-Ray Spectrometry, © Heyden & Son Ltd., 1974 and 1976, ISBN 0855010355, pp. 91-97.

*Primary Examiner* — Allen C. Ho
(74) *Attorney, Agent, or Firm* — C. Tricia Liu (57) ABSTRACT

Disclosed is a portable non-destructive testing (NDT) instrument system that transmits spectrum data measured from a test material sample to a remotely located computer for computation of the sample's atomic element composition. The atomic element composition is subsequently transmitted back to the portable instrument for display to the operator in real time. The precision and accuracy of the compositional computation is improved by the greater processing power of the high performance remote computer. The operator of the NDT instrument may choose to use the remote computer to perform part or all of the compositional computation.

20 Claims, 9 Drawing Sheets

(56) References Cited

U.S. PATENT DOCUMENTS

| | | | | |
|---|---|---|---|---|
| 8,229,064 B2* | 7/2012 | Grodzins | G01N 23/223 | 378/44 |
| 8,408,789 B2* | 4/2013 | Takahara | G01N 23/223 | 378/195 |
| 8,494,113 B2* | 7/2013 | Grodzins | G01N 23/223 | 378/44 |
| 8,515,009 B1* | 8/2013 | Piorek | G01B 15/02 | 378/45 |
| 8,548,121 B2* | 10/2013 | Sakai | G01N 23/223 | 378/44 |
| 8,611,493 B2* | 12/2013 | Hasegawa | G01N 23/223 | 378/44 |
| 8,693,625 B2* | 4/2014 | Dugas | G01N 23/223 | 378/44 |
| 8,787,523 B2* | 7/2014 | Sackett | G01N 23/223 | 378/117 |
| 8,982,338 B2* | 3/2015 | Hamilton | G01N 23/223 | 356/72 |
| 9,170,220 B2* | 10/2015 | Nishikata | G01N 23/223 | |
| 9,182,363 B2* | 11/2015 | Chen | G01N 23/223 | |
| 9,188,552 B2* | 11/2015 | Kinugasa | G01T 1/17 | |
| 9,250,201 B2* | 2/2016 | Ohashi | G01N 23/2252 | |
| 9,310,324 B2* | 4/2016 | Järvikivi | G01N 23/223 | |
| 9,400,255 B2* | 7/2016 | Nohara | G01N 23/223 | |
| 9,410,906 B2* | 8/2016 | Hirose | H05G 1/025 | |
| 9,448,190 B2* | 9/2016 | Yun | G01N 23/2076 | |
| 9,449,781 B2* | 9/2016 | Yun | H01J 35/08 | |
| 9,570,265 B1* | 2/2017 | Yun | H01J 35/14 | |
| 9,594,036 B2* | 3/2017 | Yun | G01N 23/223 | |
| 9,594,037 B2* | 3/2017 | Mizuno | G01T 7/04 | |
| 9,683,953 B2* | 6/2017 | Jones | G01N 23/223 | |
| 9,739,730 B2* | 8/2017 | Hegeman | G01N 23/223 | |
| 9,746,433 B2* | 8/2017 | Yamada | G01N 23/223 | |
| 9,778,213 B2* | 10/2017 | Bakeman | G01N 23/223 | |
| 9,778,214 B2* | 10/2017 | Sako | G01N 23/223 | |
| 9,784,700 B2* | 10/2017 | Sakuta | G01N 23/223 | |
| 9,791,392 B2* | 10/2017 | Yagi | G01N 23/223 | |
| 9,791,393 B2* | 10/2017 | Sako | G01N 23/223 | |
| 9,810,648 B2* | 11/2017 | Takahara | G01N 23/223 | |
| 9,810,649 B2* | 11/2017 | Takahara | G01N 23/223 | |
| 9,829,447 B2* | 11/2017 | Yagi | G01N 23/223 | |
| 9,829,448 B2* | 11/2017 | Wormington | G01N 23/223 | |

* cited by examiner

XRF/XRD SYSTEM WITH DYNAMIC MANAGEMENT OF MULTIPLE DATA PROCESSING UNITS

FIELD OF THE INVENTION

The present disclosure relates to portable x-ray fluorescence (XRF) analytical inspection instruments, and more particularly to an instrument system which measures the elemental composition (henceforth referred to as 'chemistry') of a test sample, and which is operable by selectively transmitting measured spectrum data to a remotely located computer for remote computation of the chemistry. The chemistry result is subsequently transmitted back to the portable instrument for display to the user in real time.

BACKGROUND OF THE INVENTION

Conventional portable XRF analytical instruments consist of an emitter which emits an excitation, a sensor which senses response signals emanating from a test material sample, and a spectrum constructor which constructs a spectrum of the intensity vs energy or wavelength of the response signals. The spectrum is converted to the sample's chemistry by a series of computationally intensive algorithms, and then rendered on the display of the portable instrument.

In the case of an energy dispersive XRF device, the spectrum is a histogram of the energy levels sensed by the X-ray detector during the measurement process. In the case of optical sensor-based instruments, such as Laser Induced Breakdown Spectroscopy (LIBS) and Near Infrared Spectroscopy (NIRS), among others, the spectrum is a histogram of the wavelengths of the electromagnetic energy emanating from the test material sample.

The primary purpose for using such analytical instrument technologies is to quickly and accurately determine the chemistry of a material test sample in order to classify it qualitatively or quantitatively. A qualitative classification indicates that one or more atomic elements of interest are present in a material test sample. A quantitative classification indicates the concentration of one or more atomic elements of interest that are present in a material test sample. For optimal inspection productivity, and to reduce measurement variability, it is important to minimize the time interval between the start of a measurement cycle and its end when the chemistry result is displayed. This has been a long standing challenge for designers of analytical portable instruments.

Presently, all of the signal processing required to derive chemistry information from a raw spectrum is performed entirely within the portable instrument. This is hereafter referred to as "on-board" processing. In on-board processing, the signal processing performance is not optimal due to the practical constraints associated with a portable instrument, such as power consumption and electronics packaging space. Accordingly, the limits placed on the speed and amount of signal processing required for producing a highly accurate chemistry result cause conventional instruments to be far from optimal as compared to what could be achieved if such constraints did not exist.

SUMMARY OF THE INVENTION

It is the general object of the present disclosure to overcome the problems associated with background art by introducing an instrument system with a substantially improved measurement chemistry result that can be displayed to the user of a portable analytical instrument in real time.

More specifically, the general object of the present disclosure is to improve the speed, precision and accuracy of the chemistry calculation performed on the spectrum data acquired by the portable instrument from a test sample material. This is achieved by transmitting the spectrum data to a high performance remote computer in order to perform the intensive signal processing required to determine the sample's chemistry with a high degree of fidelity, and then returning the result to the portable instrument to be displayed in real time without any noticeable delay. (i.e. The complete measurement cycle should be less than about one second). This method of transmitting data to a high performance remote computer is hereafter referred to as "remote" or "off-board" processing, the two terms being used interchangeably.

The foregoing and other objects of the present disclosure may be realized with a portable instrument, a remote computing capability, a communication interface that can be wireless or have a physical cable connection, and a means to apply spectrum processing and/or chemistry conversion outside of the portable instrument. The remote computing capability may include connection to a specific computer or connection via internet to distributed computation capability hereafter referred to as "the Cloud".

In accordance with various embodiments of the invention, disclosed is an arrangement of an analog to digital converter (ADC), a spectrum constructor, an on-board data processing unit having two or more operation modes, and having physical or wireless data connections with one or more remote computers, including computers located in the Cloud. The on-board data processing unit is thereby able to take advantage of the increased processing power of remote computers during measurement of the chemistry of a material sample. The primary object of the present disclosure is to outsource the hardware limitations of a portable instrument to a computer system of greater processing power.

DETAILED DESCRIPTION OF THE INVENTION

Figure 1:
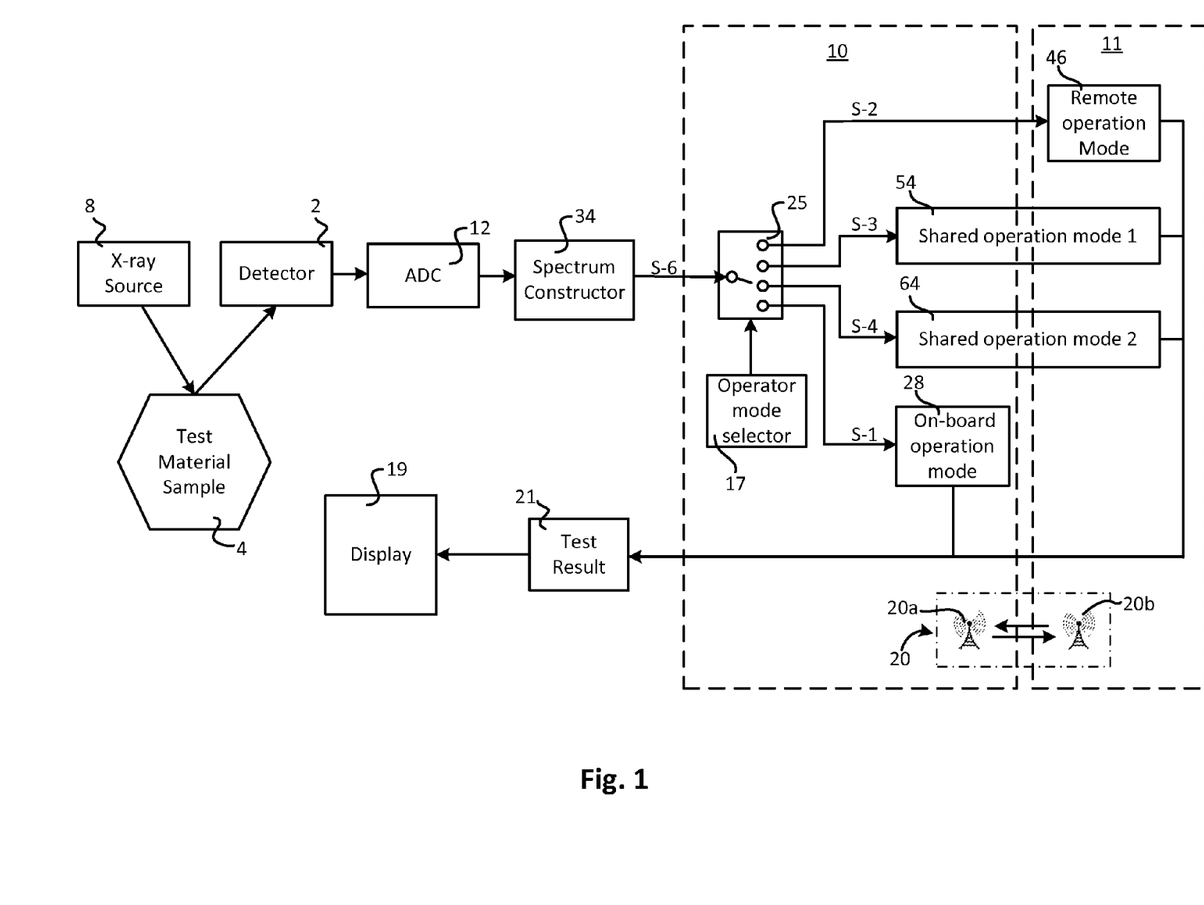
FIG. 1 is a schematic view of the preferred embodiment according to the present disclosure.

FIG. 1 illustrates an X-ray analytical system according to the present disclosure, the system typically being used for chemical composition analysis. The system comprises a portable X-ray analytical instrument (not shown), an X-ray source 8 emitting X-rays, a test material sample 4, a detector 2, an analog to digital converter (ADC) 12, a spectrum constructor 34, an on-board data processing unit 10, an off-board data processing unit 11, and a display 19 for displaying a test result 21. The X-ray analytical system of FIG. 1 has various operation modes, optionally including an on-board operation mode 28, a remote operation mode 46, a first shared operation mode 54 and further optionally a second shared operation mode 64. Spectrum constructor 34 can be configured using any commonly known method and instrumentation components and structure, such as that explained in "An Introduction to X-Ray Spectrometry", section 4.3.7, "Typical instrumentation for analysis with a crystal spectrometer" by Ron Jenkins (later as Jenkins), © Heyden & Son Ltd., 1974 and 1976, ISBN 0855010355, pp 91-97. Commonly used electronic components and structures are also known to implement the teachings of Jenkins. On-board data processing unit 10 includes an operator mode selector 17 acting on a logical mode switch 25. Data from spectrum constructor 34 is passed to logical mode switch 25 via data path S-6. Logical mode switch 25 directs the data to the one selected operation mode 28, 46, 54 or 64 via the corresponding data path S-1, S-2, S-3 or S-4.

The portable X-ray analytical instrument performs a measurement cycle by exposing test material sample 4 to the output of X-ray source 8 and detecting the resulting response with detector 2. The output signal of detector 2 is provided to ADC 12, the output of which is sent to spectrum constructor 34, which is a fast processor such as a Field Programmable Gate Array (FPGA) programmed to produce a spectrum from the data acquired during the measurement. Depending on operator mode selection 17, processing of the output from spectrum constructor 34 is accomplished either by on-board operation mode 28, or by remote operation mode 46, or by first shared operation mode 54, or by second shared operation mode 64. It should be noted that "operator mode selection 17", is a self-explanatory term, and in the context of the essence of the novel aspects of the present disclosure, denotes allowing the operator to select the mode of operation: namely, which shared operation mode is preferable for a specific test. Operator mode selection 17 may be constructed to allow the operator to make a selection using many commonly known components, such as a virtual button on a screen, or a physical button or switch. Complex and computationally intensive algorithms, well known to those skilled in the art, are required to derive the chemistry of test material sample 4 from the spectrum created by spectrum constructor 34. Steps in deriving the chemistry of test material sample 4 may include application of calibration data for the particular portable instrument being used, application of algorithms to correct for the effect of the sample matrix on the elemental data in the spectrum, or comparison of processed elemental data with known material compositions to identify the material of the test material sample 4. As disclosed in the various embodiments of the present invention, depending on operator selection, all these steps may be performed on-board the portable instrument, or they may all be performed remotely, or the steps may be shared in various ways between the portable instrument and the remote computing capability.

Also shown in FIG. 1 is a two-way data transmission system 20 transmitting data between on-board data processing unit 10 and off-board data processing unit 11. The data transmission system comprises a pair of transceivers 20a and 20b, which may receive and transmit data wirelessly or via a physical data connection. Two-way data transmission system 20 enables exchange of information between on-board data processing unit 10 and off-board data processing unit 11 by means of a standard wireless interface, such as WLAN or Bluetooth, or by means of a physical data connection, which may consist of a cable with a standard data transfer interface, such as USB, Ethernet or RS232. When a description of an embodiment refers to either the wireless or the cable connection, it is intended to denote that the other may be used if necessary or desired.

It should be noted that the signals exchanged between on-board data processing unit 10 and off-board data processing unit 11 can pass through a network router, a smart phone, or other intermediary device present in the communication path, and such intermediary devices are within the scope of the present disclosure.

It should be herein noted that one of the most important novel aspects of the present disclosure is to utilize a means of logical mode selection, such as logical mode switch 25, to allow the selection among at least two operational modes, each having different ways of splitting the task of spectrum processing and conversion to chemistry between a handheld X-ray analytical instrument and a remote computer.

Another novel aspect of the present disclosure is to allow operators to determine the selection mode based on the factors of inspection setup, i.e., the available data speed of two-way data transmission system 20, the required resolution and accuracy of the analysis and the required speed of the measurement cycle.

Although the teachings in the present disclosure apply to any portable X-ray or optical analytical instrument used for non-destructive testing (NDT), the exemplary embodiment described herein is an X-ray fluorescence (XRF) instrument.

A measurement cycle of the portable instrument ends when the instrument receives and displays the calculated chemical composition of test material sample 4. The measurement cycle is preferably completed in less than one second; however, users may set a longer time if they wish to obtain a more accurate chemistry result.

Figure 2A:
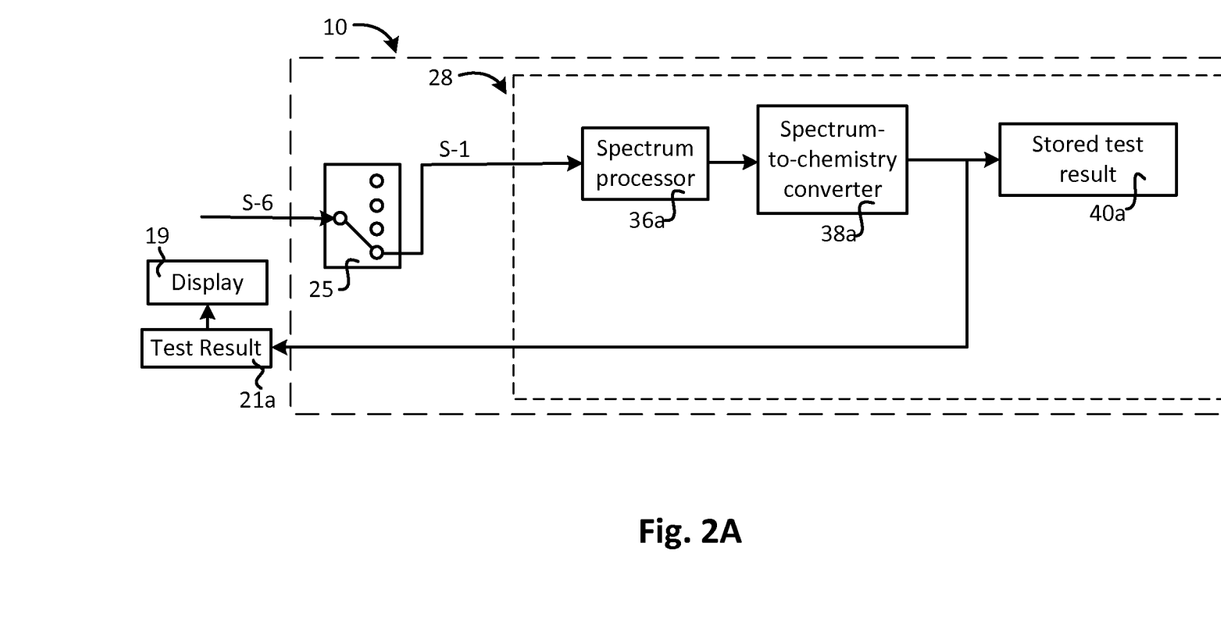
FIG. 2A is a schematic view of the embodiment with regular on-board data processing selected according to the present disclosure.

Referring again to FIG. 1, when on-board operation mode 28 is selected, spectrum processing and conversion to chemistry are all performed by on-board data processing unit 10, as further shown in FIG. 2A, in which on-board data processing unit 10 has no wireless or other remote data connections. When remote operation mode 46 is selected, spectrum processing and conversion to chemistry are all performed by off-board data processing unit 11, as further shown in FIG. 2B. When shared operation modes 54 or 64 are selected, spectrum processing and conversion to chemistry can be shared in various ways between on-board data processing unit 10 and off-board data processing unit 11. Examples of such sharing are further shown in FIGS. 2C and 2D.

It should be noted that off-board data processing unit 11 represents all possible remotely accessed computing facilities, commercially available or proprietary to a specific party. It should also be appreciated that off-board data processing unit 11 may be a stand-alone computer or may be part of the Cloud computing network, and such alternation is also within the scope of the present disclosure.

FIG. 2A shows the on-board operation mode 28 in more detail. Directed by logical mode switch 25, spectrum data from selected data path S-1 enters on-board operation mode 28. The data is processed by spectrum processor 36*a* and converted to chemistry by spectrum-to-chemistry converter 38*a*. The chemistry result is stored as stored chemistry result 40*a* and/or sent as test result 21*a* to be shown on the on-board display 19. It should be noted that when logical mode switch 25 is set to select on-board operation mode 28, the instrument is effectively a conventional XRF handheld instrument with all data processing completed on-board.

Figure 2B:
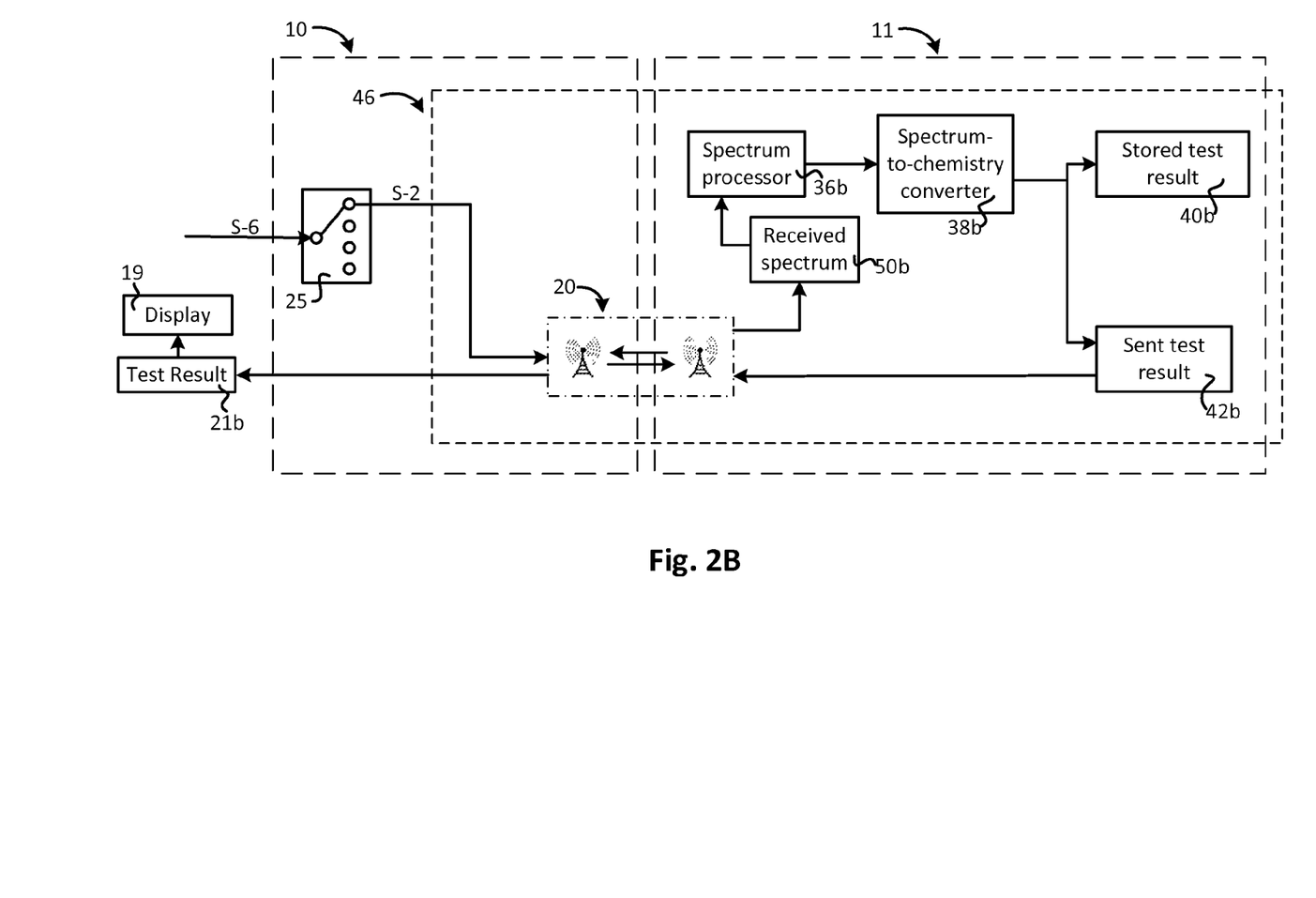
FIG. 2B is a schematic view of the embodiment wherein the remote computer performs all of the spectrum processing and conversion to chemistry according to the present disclosure.

Reference is now made to FIG. 2B, which illustrates a remote operation mode 46, which is included in both an on-board data processing unit 10 and an off-board data processing unit 11. Directed by logical mode switch 25, spectrum data from selected data path S-2 enters remote operation mode 46, and is transmitted to off-board data processing unit 11 by means of data transmission system 20. A received spectrum 50*b* is processed by a remote spectrum processor 36*b* and converted to chemistry by a remote spectrum-to-chemistry converter 38*b*. The chemistry result may be stored remotely at stored chemistry result 40*b* and/or sent as test result 21*b* to the on-board display 19 via sent test result 42*b* and data transmission system 20.

Figure 2C:
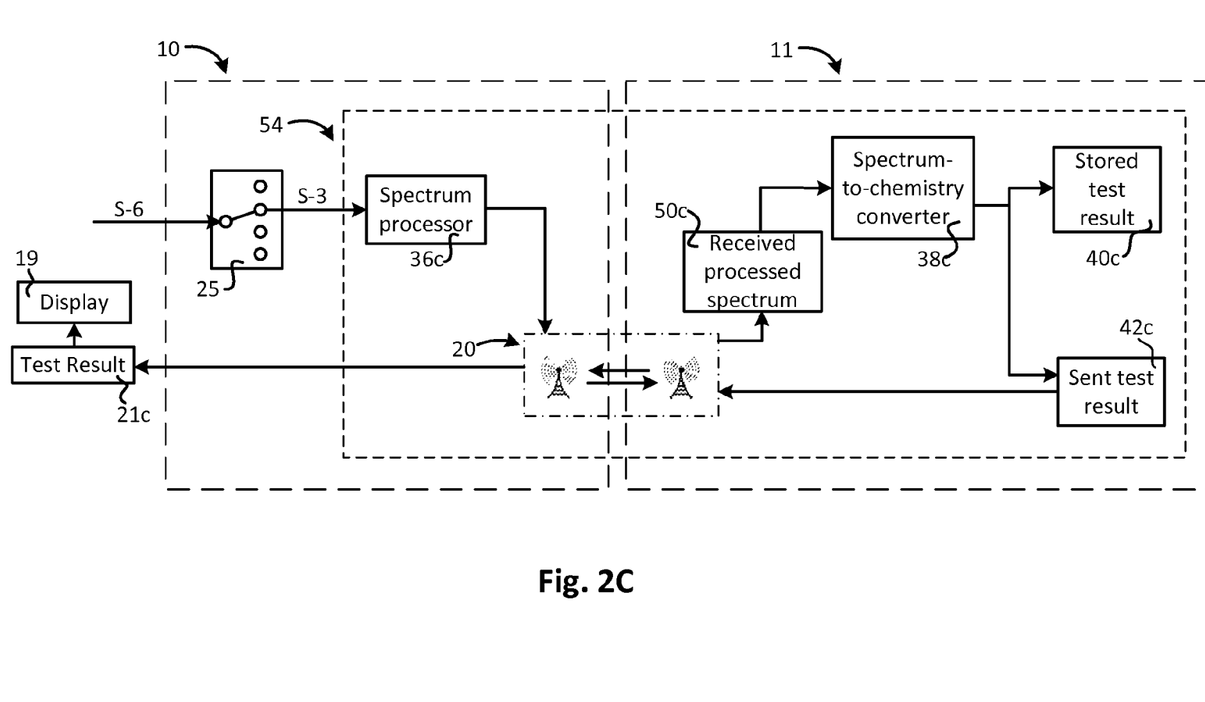
FIG. 2C is a schematic view of the embodiment where the portable instrument performs the spectrum processing and the remote computer performs the conversion to chemistry according to the present disclosure.

FIG. 2C illustrates a first method of sharing data processing, showing a first shared operation mode 54 which is included in both an on-board data processing unit 10 and an off-board data processing unit 11. Directed by logical mode switch 25, spectrum data from selected data path S-3 enters first shared operation mode 54. The data is processed by on-board spectrum processor 36*c*, and then transmitted to off-board data processing unit 11 by means of data transmission system 20. A received processed spectrum 50*c* is converted to chemistry by a remote spectrum-to-chemistry converter 38*c*. The chemistry result may be stored remotely at stored chemistry result 40*c* and/or sent as test result 21*c* to the on-board display 19 via sent test result 42*c* and data transmission system 20.

Figure 2D:
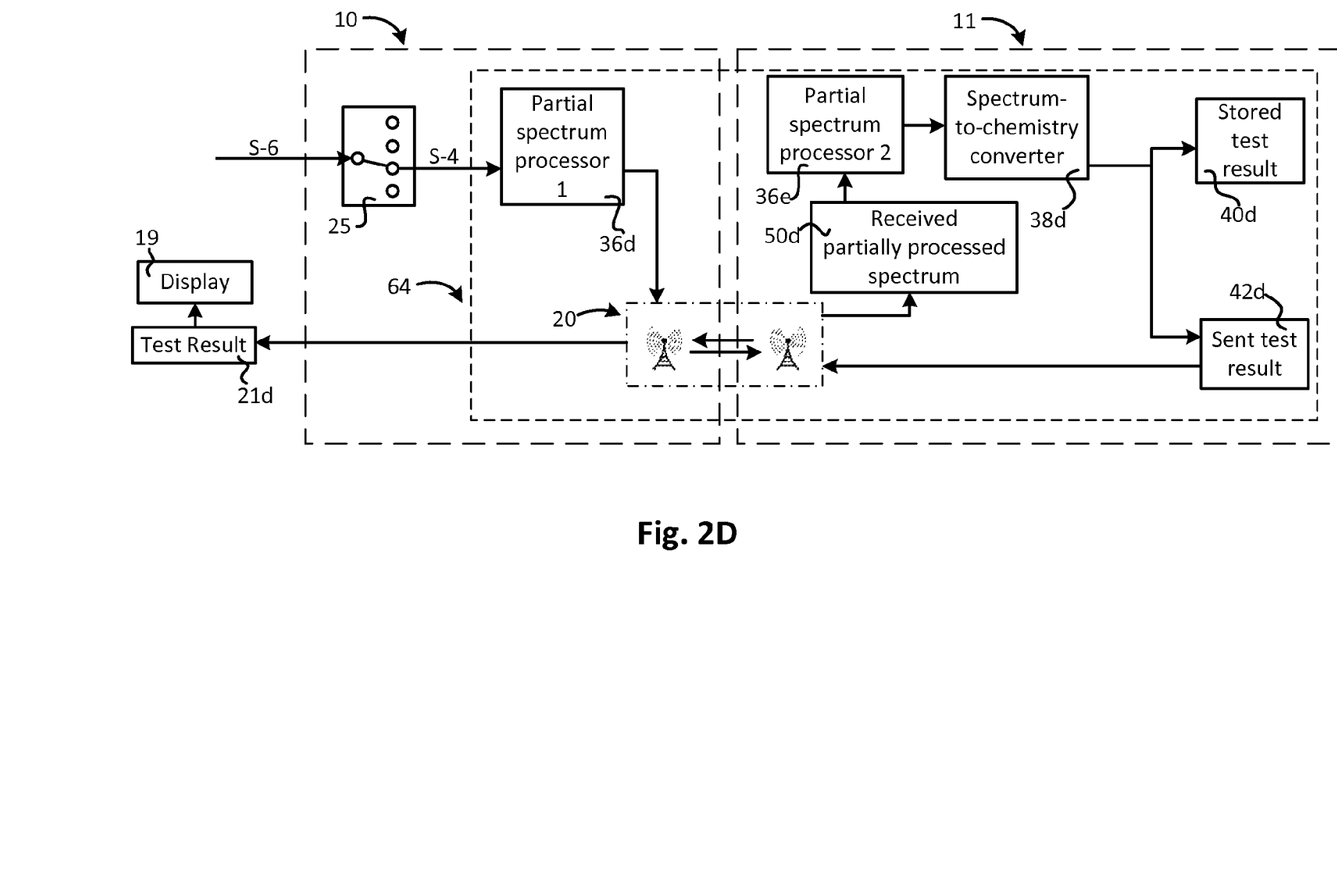
FIG. 2D is a schematic view of the embodiment where the portable instrument performs part of the spectrum processing and the remote computer completes the spectrum processing and then performs the conversion to chemistry according to the present disclosure.

FIG. 2D illustrates a second method of sharing data processing, showing a second shared operation mode 64, which is included in both an on-board data processing unit 10 and an off-board data processing unit 11. Directed by logical mode switch 25, spectrum data from selected data path S-4 enters second shared operation mode 64. Data is partially processed by on-board partial spectrum processor1 36*d*, and then transmitted to off-board data processing unit 11 by means of data transmission system 20. Data from a received partially processed spectrum 50*d* is passed to partial spectrum processor2 36*e* where spectrum processing is completed. The processed spectrum is then converted to chemistry by a remote spectrum-to-chemistry converter 38*d*. The chemistry result may be stored remotely at stored chemistry result 40*d* and/or sent as test result 21*d* to the on-board display 19 via sent test result 42*d* and data transmission system 20.

It should be noted that spectrum processors 36*a*, 36*b*, 36*c*, 36*d*, and 36*e* preferably use different algorithms for processing, with some requiring less and some requiring more computing power, yielding results of less or more accuracy, respectively. Typically, on-board spectrum processors such as 36*a*, 36*c* and 36*d* have algorithms yielding less accuracy while requiring less computing power. Remote spectrum processors such as 36*b* and 36*e* have algorithms yielding more accuracy while requiring more computing power. Similarly, corresponding spectrum-to-chemistry converters 38*a*, 38*b*, 38*c*, and 38*d* are also preferably configured to use different algorithms with some requiring less and some requiring more computing power, yielding results of less or more accuracy, respectively. As such, on-board spectrum converters such as 38*a* have algorithms yielding less accuracy while requiring less computing power. Remote spectrum converters such as 38*b*, 38*c* and 38*d* have algorithms yielding more accuracy while requiring more computing power. This is yet another novel aspect of the present disclosure which allows operators the freedom to choose algorithms and computing power suited to the requirements for speed and accuracy of the specific NDT test procedure.

In addition, spectrum processors 36*a*, 36*b*, 36*c*, 36*d*, and 36*e*, and corresponding spectrum-to-chemistry converters 38*a*, 38*b*, 38*c*, and 38*d*, are depicted as separate functional blocks in FIGS. 2A-2D. However, each spectrum processor and its corresponding converter can be within the same or separate integrated circuit. Both of these embodiments are within the scope of the present disclosure.

Figure 3A:
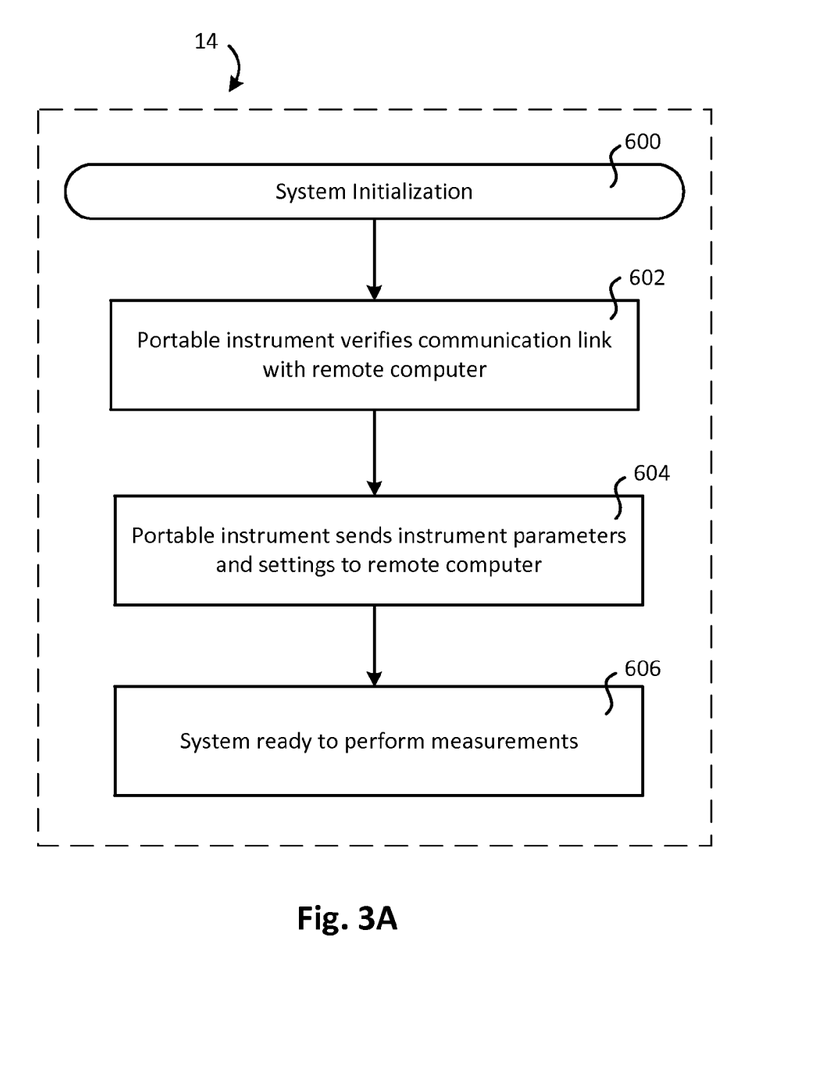
FIG. 3A is a flow chart showing initialization of the communication between the portable instrument and a remote computer.

FIG. 3A is a flow chart which describes an initialization process 14, comprising steps of setting up the portable instrument to operate with remote communication capability. In step 600, both the portable instrument and the remote computer are initialized. In step 602, the portable instrument verifies its communication link with off-board data processing unit 11. In step 604, the portable instrument's parameters and settings are sent to off-board data processing unit 11, and in step 606 the portable instrument is ready to perform measurements with both on-board and remote data analysis capability.

Figure 3B:
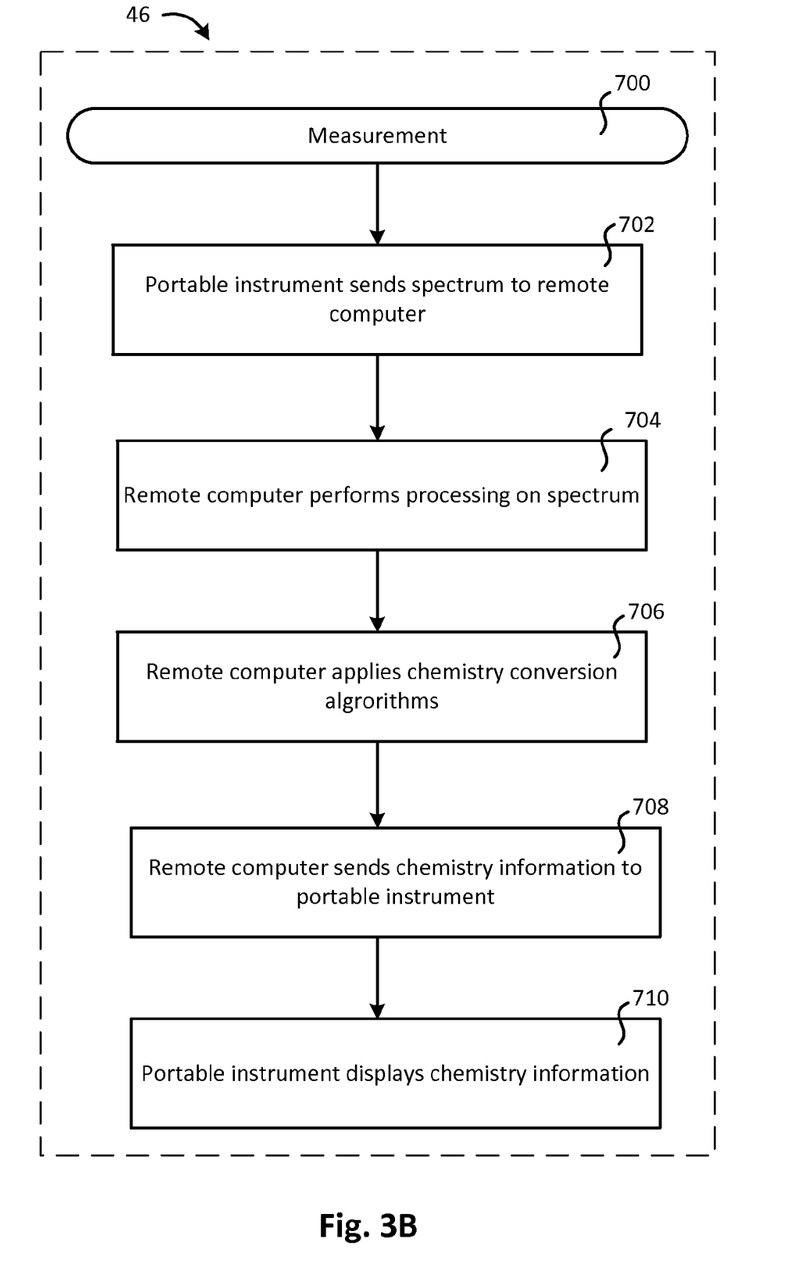
FIG. 3B is a flow chart of the embodiment where the remote computer performs all of the spectrum processing and conversion to chemistry.

FIG. 3B, which should be viewed in conjunction with FIG. 2B, is a flow chart describing the steps of performing remote spectrum processing and chemistry conversion with remote operation mode 46. In step 700, the portable instrument performs a measurement on test material sample 4, and in step 702 it sends the resulting spectrum to off-board data processing unit 11. In step 704, the remote computer performs processing on the spectrum, and in step 706, the remote computer applies chemistry conversion algorithms to the spectrum. In step 708, the remote computer sends the results back to the portable instrument, and in step 710, the portable instrument displays the chemistry information of test material sample 4.

Figure 3C:
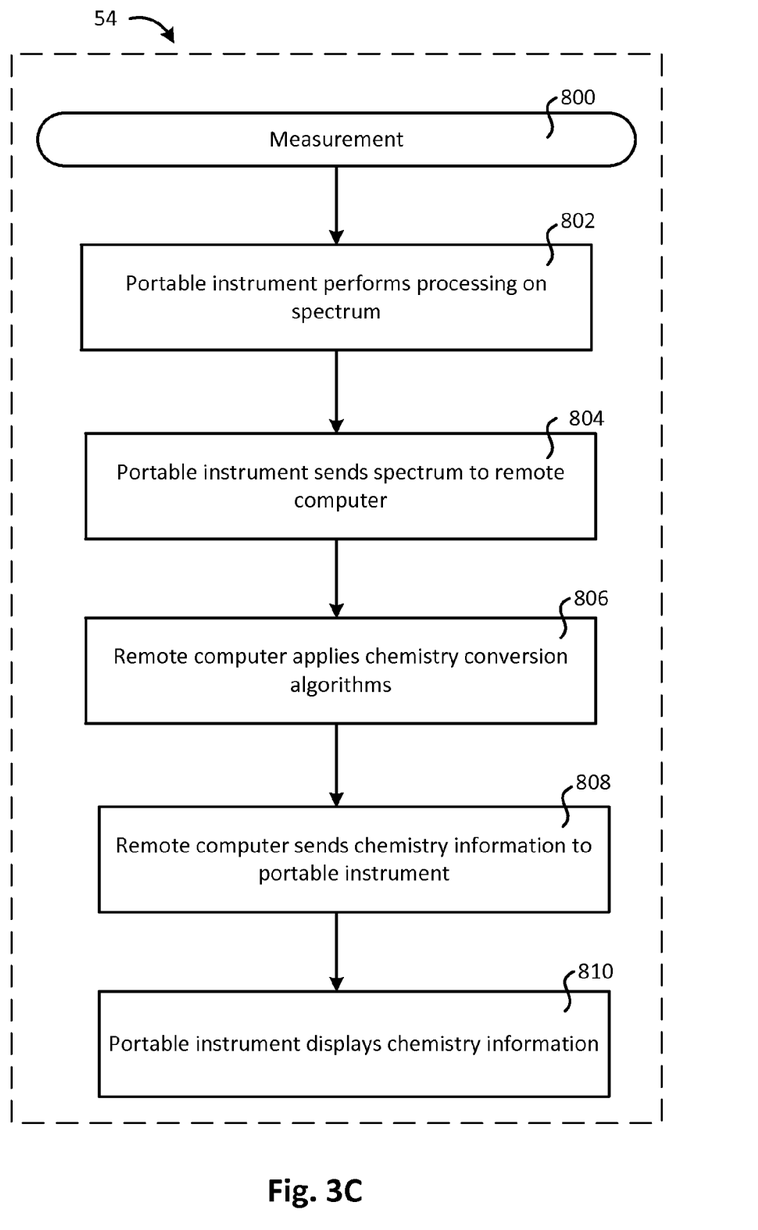
FIG. 3C is a flow chart of the embodiment where the portable instrument performs the spectrum processing and the remote computer performs the conversion to chemistry.

FIG. 3C, which should be viewed in conjunction with FIG. 2C, is a flow chart describing the steps of a first embodiment of performing shared spectrum processing and chemistry conversion with first shared operation mode 54. In step 800, the portable instrument performs a measurement on test material sample 4, and in step 802 it performs on-board processing of the resulting spectrum. In step 804 the portable instrument sends the processed spectrum to off-board data processing unit 11. In step 806, the remote computer applies chemistry conversion algorithms to the spectrum. In step 808, the remote computer sends the results back to the portable instrument, and in step 810, the portable instrument displays the chemistry information of test material sample 4.

Figure 3D:
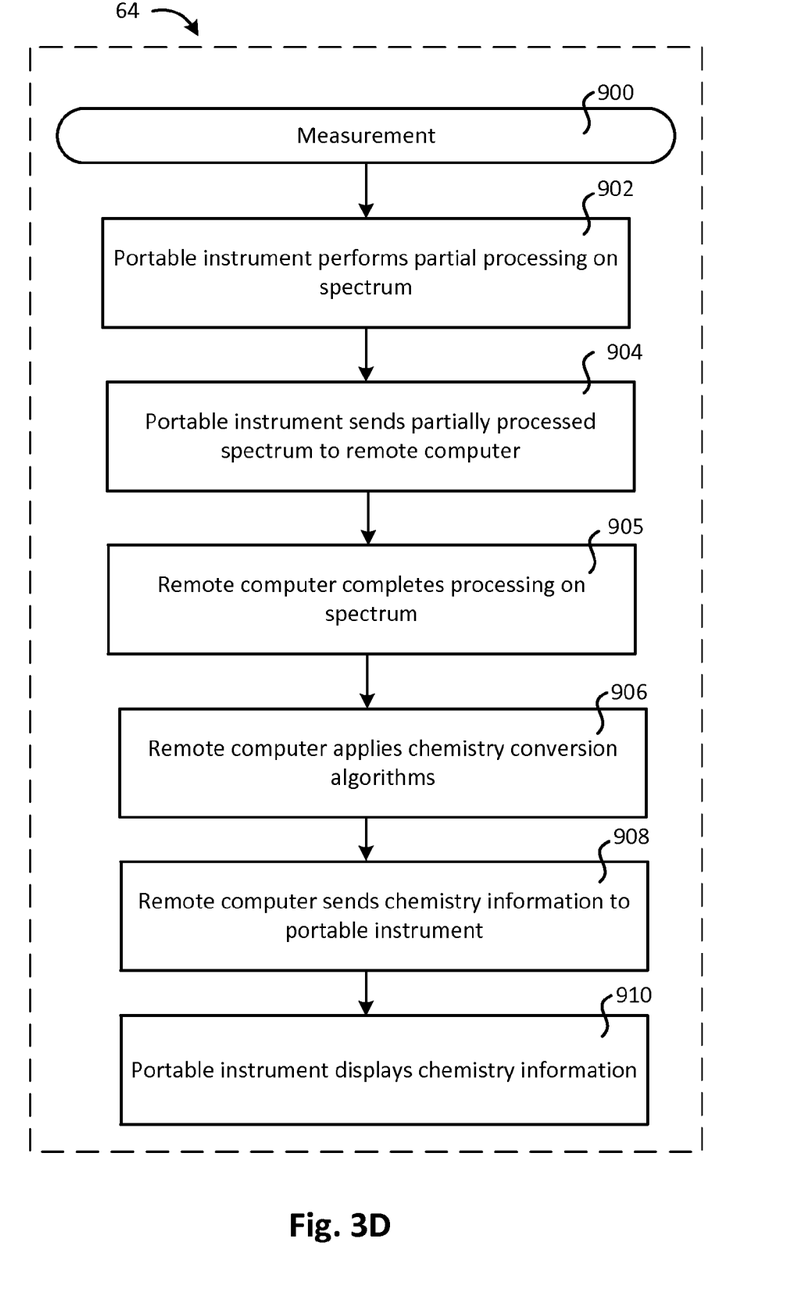
FIG. 3D is a flow chart of the embodiment where the portable instrument performs part of the spectrum processing and the remote computer completes the spectrum processing and then performs the conversion to chemistry.

FIG. 3D, which should be viewed in conjunction with FIG. 2D, is a flow chart describing the steps of a second embodiment of performing shared spectrum processing and chemistry conversion with second shared operation mode 64. In step 900, the portable instrument performs a measurement on test material sample 4, and in step 902 it performs partial on-board processing of the resulting spectrum. In step 904 the portable instrument sends the partially processed spectrum to off-board data processing unit 11. In step 905 the remote computer completes processing of the spectrum, and in step 906 the remote computer applies chemistry conversion algorithms to the processed spectrum. In step 908, the remote computer sends the results back to the portable instrument, and in step 910, the portable instrument displays the chemistry information of test material sample 4.

Although the present invention has been described in relation to particular embodiments thereof, many other variations and modifications and other uses will become apparent to those skilled in the art. It is preferred, therefore, that the present invention not be limited by the specific disclosure herein.

What is claimed is:

1. An X-ray analytical system for testing and analyzing chemical composition and/or atomic structure of a sample during a testing session, the X-ray analytical system comprising:
a portable X-ray analytical instrument for testing and analyzing chemical composition and/or atomic structure of a sample;
an off-board data processing unit situated off-board separately from the portable X-ray analytical instrument;
wherein the portable X-ray analytical instrument comprises;
an X-ray source configured to emit a beam of X-rays onto a sample;
a detector configured to detect received X-rays returned from the sample;
a spectrum constructor constructing a raw spectrum from the received X-rays;
an on-board data processing unit,
wherein the on-board data processing unit and the off-board data processing unit are configured in unison to complete at least two processing tasks, which collectively process an entire processing task of processing the raw spectrum to produce a test result for display on the portable X-ray analytical instrument;
a display configured to display the test result; and
wherein the on-board processing unit further comprises:
a mode switch; and
an operator mode selector connected to and instructing the mode switch to switch between at least two operation modes, wherein each of the at least two operation modes defines how the entire processing task is distributed between the at least two processing tasks.

2. The X-ray analytical system of claim 1, wherein the X-ray analytical system further includes a data transmission system comprising a first transceiver on the on-board data processing unit, and a second transceiver on the off-board data processing unit, the data transmission system thereby allowing two-way communication between the off-board data processing unit and the on-board data processing unit.

3. The X-ray analytical system of claim 2, wherein the data transmission system is configured to be a wireless transmission system, and the first transceiver is a first wireless transceiver and the second transceiver is a second wireless transceiver.

4. The X-ray analytical system of claim 2, wherein the entire processing task further includes spectrum processing, spectrum to chemistry converting and test result forming.

5. The X-ray analytical system of claim 4, wherein the at least two processing tasks include an on-board processing task being performed by the on-board processing unit, and an off-board processing task being performed by the off-board processing unit.

6. The X-ray analytical system of claim 5, wherein the operator mode selector instructs the mode switch to switch to an operation mode in which the on-board processing task includes all of the at least two processing tasks and the off-board processing task is nil.

7. The X-ray analytical system of claim 6, wherein the data transmission system is not activated during the testing session.

8. The X-ray analytical system of claim 5, wherein the operator mode selector instructs the mode switch to switch to an operation mode in which all of the off-board processing task includes all of the at least two processing tasks and the on-board processing task is nil.

9. The X-ray analytical system of claim 8, wherein the data transmission system transmits the raw spectrum from the on-board data processing unit to the off-board data processing unit, and the data transmission system subsequently transmits at least part of the testing result from the off-board data processing unit to the on-board data processing unit for displaying the test result on the display.

10. The X-ray analytical system of claim 5, wherein the operator mode selector instructs the mode switch to switch to an operation mode in which the on-board processing task is the spectrum processing, and the off-board processing task is the spectrum to chemistry converting and test result forming.

11. The X-ray analytical system of claim 10, wherein the data transmission system transmits a data set from the spectrum processing from the on-board data processing unit to the off-board data processing unit, and the data transmission system subsequently transmits at least part of the testing result from the off-board data processing unit to the on-board data processing unit for displaying the test result on the display.

12. The X-ray analytical system of claim 11, wherein the data transmission system is configured so that the first transceiver and the second transceiver establish data communication with each other prior to the testing session.

13. The X-ray analytical system of claim 5, wherein the operator mode selector instructs the mode switch to switch to an operation mode in which the on-board processing task includes a first part of the spectrum processing, and the off-board processing task includes a second part of the spectrum processing, and wherein the first part and the second part of the spectrum processing collectively constitute the entire spectrum processing.

14. The X-ray analytical system of claim 13, wherein the off-board processing task includes conversion to chemistry.

15. The X-ray analytical system of claim 14, wherein the data transmission system transmits a data set from the first part of the spectrum processing from the on-board data processing unit to the off-board data processing unit, and the data transmission system subsequently transmits at least part of the testing result from the off-board data processing unit to the on-board data processing unit for displaying the test result on the display.

16. The X-ray analytical system of claim 15, wherein the data transmission system is configured so that the first transceiver and the second transceiver establish data communication with each other prior to the testing session.

17. The X-ray analytical system of claim 1, wherein the off-board data processing unit is not integrally packaged together with the portable X-ray analytical instrument and is at any distance from the portable instrument.

18. The X-ray analytical system of claim 1, wherein the detector produces electronic analog pulses, one pulse for each X-ray received, wherein the amplitude of each pulse is proportional to the energy of the corresponding X-ray.

19. The X-ray analytical system of claim 18, wherein the portable X-ray analytical instrument further comprises an analog to digital converter converting the electronic analog pulses to digital data.

20. The X-ray analytical system of claim 18, wherein the spectrum constructor is a fast spectrum constructor which constructs a spectrum of the number of pulses received within each X-ray energy range.

* * * * *